United States Patent [19]

Fabo

[11] Patent Number: 5,635,201
[45] Date of Patent: Jun. 3, 1997

[54] METHOD AND AN ARRANGEMENT FOR MANUFACTURING WOUND DRESSINGS, AND A WOUND DRESSING MANUFACTURED IN ACCORDANCE WITH THE METHOD

[75] Inventor: Tomas Fabo, Mölnlycke, Sweden

[73] Assignee: Molnlycke AB, Goteborg, Sweden

[21] Appl. No.: 302,875

[22] PCT Filed: Mar. 30, 1993

[86] PCT No.: PCT/SE93/00270

§ 371 Date: Sep. 14, 1994

§ 102(e) Date: Sep. 14, 1994

[87] PCT Pub. No.: WO93/19709

PCT Pub. Date: Oct. 14, 1993

[30] Foreign Application Priority Data

Mar. 30, 1992 [SE] Sweden .................. 9200983

[51] Int. Cl.$^6$ .................................................. A61F 13/00
[52] U.S. Cl. .................. 424/443; 424/449; 427/2.31; 427/348; 602/47
[58] Field of Search ........................... 424/443, 449; 427/2.31, 348; 602/47

[56] References Cited

U.S. PATENT DOCUMENTS

| 3,042,549 | 7/1962 | Arnold et al. | 117/140 |
| 3,697,473 | 10/1972 | Polmanteer et al. | 260/37 |
| 4,175,557 | 11/1979 | Hung | 128/156 |
| 4,661,099 | 4/1987 | von Bittera et al. | 604/290 |
| 4,684,538 | 8/1987 | Klemarczyk | 427/54.1 |
| 4,684,557 | 8/1987 | Pennace et al. | 428/447 |
| 4,690,683 | 9/1987 | Chien et al. | 604/896 |
| 4,838,253 | 6/1989 | Brassington et al. | 604/304 |
| 5,322,729 | 6/1994 | Heeter | 428/306.6 |

FOREIGN PATENT DOCUMENTS 0251810   1/1988   European Pat. Off. .

*Primary Examiner*—D. Gabrielle Phelan
*Attorney, Agent, or Firm*—Young & Thompson

[57] ABSTRACT

A method and apparatus for manufacturing a wound dressing, and a wound dressing produced thereby. The upper surface of a perforated carrier material (2) is coated with a curable silicone mixture (3) and cold air is blown onto the underside of the coated carrier material. Heat is then applied to the silicone mixture until it has cured to a silicone gel.

14 Claims, 1 Drawing Sheet

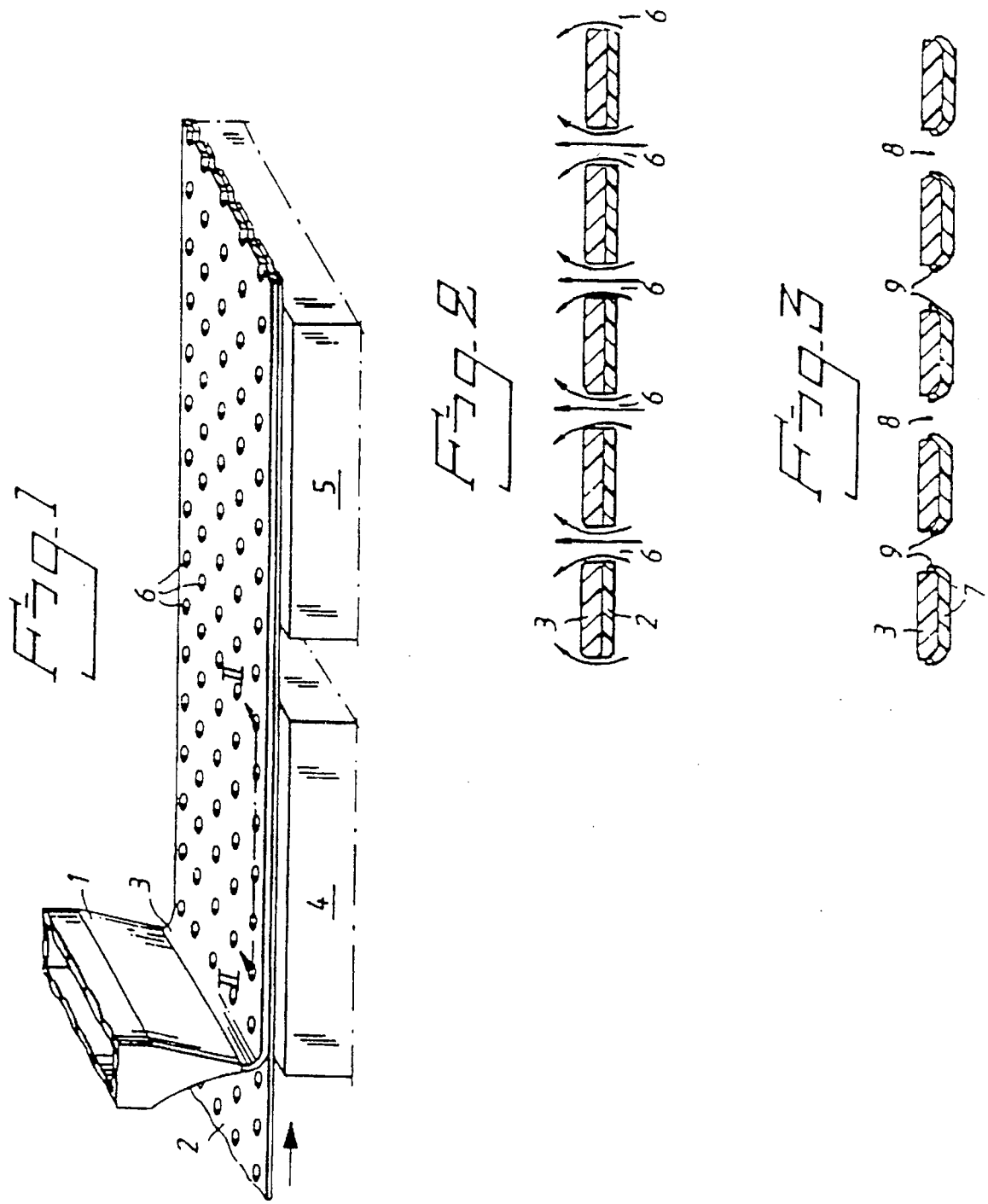

METHOD AND AN ARRANGEMENT FOR MANUFACTURING WOUND DRESSINGS, AND A WOUND DRESSING MANUFACTURED IN ACCORDANCE WITH THE METHOD

FIELD OF THE INVENTION

The present invention relates to a method and to an arrangement of apparatus for manufacturing wound dressings of the kind which comprise a perforated carrier material and a layer of hydrophobic silicone gel which lies against the wound, or sore, when the dressing is worn. The invention also relates to a wound dressing manufactured in accordance with the inventive method.

BACKGROUND OF THE INVENTION

A wound dressing of this kind is known from our European Patent No. 0,261,167, in which the carrier material is fully enclosed by the silicone gel although while leaving openings through the dressing. When manufacturing a dressing of this kind, the carrier material is dipped into a mixture of those components which, when cured, form the hydrophobic silicone gel, and the carrier material is then transferred to a curing oven in which the carrier material is cured. In order to ensure that the silicone gel is uniformly distributed on both sides of the carrier material and that the perforations do not become clogged with gel, the carrier material is guided in the oven in a relatively complicated path. This known method is not suited to high production rates.

SUMMARY OF THE INVENTION

The object of the present invention is to provide a method which will enable such wound dressings to be manufactured at a high production rate and in a simple and reliable manner.

The invention also relates to apparatus for carrying out the method and to a wound dressing suitable for manufacture by means of the inventive method.

To this end, an inventive method is characterized by applying a coating of a thermosetting silicone mixture to the upper surface of a perforated carrier material; blowing cold air onto the undersurface of the coated carrier material; and then applying heat to the silicone mixture until it has cured. The cold air blown onto the underside of the carrier material acts to blow the thick, viscous silicone mixture away from the perforations in the carrier material, so as to form through penetrating perforations and also to prevent clogging of the perforations in said carrier material. At the same time, the cold air flow ensures that the silicone mixture will not begin to cure before it has time to spread over the carrier material. The flow of air through the carrier material will, of course, also prevent the silicone mixture from running through the perforations in said material.

Apparatus for carrying out the aforedescribed method is characterized in that it includes means for coating the upper surface of the carrier material with a mixture of components which, when cured, form a silicone gel; an air-blowing unit for blowing cold air onto the underside of the carrier material, which is placed opposite the coating means, and means for delivering heat to the component mixture subsequent to having applied said mixture to the upper surface of the carrier material.

A wound dressing suited for manufacture by means of the aforesaid method is characterized in that the carrier material is impervious to air and fluid or only slightly permeable to air and fluid in the parts thereof lying between the perforations; and in that the carrier material has a silicone gel coating on solely one side thereof.

BRIEF DESCRIPTION OF THE DRAWINGS

The invention will now be described in more detail with reference to an exemplifying embodiment thereof and also with reference to the accompanying drawings, in which FIG. 1 is a schematic perspective view of part of an inventive arrangement for manufacturing a wound dressing and also illustrates an exemplifying embodiment of an inventive wound dressing manufactured by means of said arrangement;

FIG. 2 is a cross-sectional view taken on the line II—II in FIG. 1; and

FIG. 3 is a cross-sectional view of another exemplifying embodiment of an inventive wound dressing.

DETAILED DESCRIPTION OF THE INVENTION

FIG. 1 illustrates schematically part of an arrangement for manufacturing an inventive wound or sore dressing. The arrangement includes a unit in the form of an extruder nozzle 1 for coating a perforated carrier material 2 with a thermosetting silicone mixture 3 which includes components which when cured form a chemically cross-linked, sticky silicone gel, for instance the silicone gel which is retailed by Dow Corning and specified in the aforesaid European Patent No. 0,261,167, or the silicone gel retailed by Wacker Chemie GmBH and designated Wacker RTV-2, VP7612. The carrier material 2 is moved in the direction shown by the arrow in FIG. 1, by means not shown. These means may conveniently comprise a belt conveyor, a stentor means, to which the long side edges of the carrier material are attached, or some like means. Mounted beneath the movement path of the carrier material is an air-blowing unit 4, which extends from the nozzle 4 to a point located slightly downstream thereof. A further air-blowing unit 5 is also mounted beneath the movement path of the carrier material 2, downstream of the blower unit 4.

The arrangement operates in the following manner:

The perforated carrier material 2 is unrolled onto a conveyor, preferably from a storage reel, and is moved by the conveyor under the extruder nozzle 1 by means of which the carrier material is coated with the thermosetting silicone mixture 3, which prior to curing has the consistency of a thick, viscous fluid. Cold air is blown onto the underside of the carrier material with the aid of the unit 4 and the air flows through the perforations 6 in the carrier material, as illustrated with arrows in FIG. 2, and blows away the silicone mixture in the regions above the perforations, so as to provide through penetrating holes in the silicone mixture. The carrier material 2 coated with silicon mixture 3 is then moved to a position above the blower unit 5, which blows hot air onto the underside of the carrier material. The silicone mixture will then begin to cure in the regions around the perforations, where the exchange of heat is greatest. When the regions around the perforations have cured sufficiently, the supply of hot air is preferably cut-off and the carrier material coated with said silicone mixture is passed into a curing oven.

Hot air shall not be blown onto the carrier material in the initial stage of the manufacturing process, since it is necessary for the silicone mixture to spread and be properly dispersed over the carrier material before the curing process begins. It is also important that the nozzle 4 is not heated, since this will incur the risk of the nozzle becoming blocked or clogged.

In order to prevent the silicone mixture from being blown from the carrier material, it is essential that the carrier material is impervious to air, or at least so impervious that essentially all air will flow through the perforations. However, material which permits air to diffuse therethrough can be used beneficially when practicing the invention. The carrier material shall also be impervious to fluid, or at least have a fluid-permeability which is so low that the thick-viscous fluid, i.e. the silicone mixture prior to curing, is unable to run therethrough.

Suitable carrier materials are relatively soft plastic sheets, such as polyethylene, polyamide, polyurethane, silicone film, etc.

The plastic sheet may also be microporous, i.e. have a sufficiently low fluid and air-permeability to satisfy the aforesaid requirements, so as to present a large surface area for adhesion between plastic sheet and silicone mixture. In order to ensure good adherence between silicone gel and plastic sheet, the plastic sheet may be coated with a silicone primer, for instance with Dow Corning 355 Medical Adhesive.

Another method of ensuring good adherence between silicone gel and carrier material is to use a perforated two-ply material as the carrier material. This two-ply material may, for instance, consist of a laminate which comprises a plastic sheet and a layer of non-woven or textile material which can be laminated with the aid of heat or a binding agent. The two-layer material may also be comprised of a coated fibre material having a plastic film moulded on one side thereof.

That side of the carrier material which is not coated with silicone gel will preferably have a uniform and smooth surface, so as to have low adherence to any dried wound fluid which may have exuded through the perforations as the dressing is worn. This is particularly important when the dressing is used together with an overlying absorbent body or pad, since it must be possible to remove the absorbent body without the dressing being disturbed as a result of wound fluid that has dried on the absorbent body adhering to the carrier material and entraining the material in the initial stages of removing the absorbent body.

FIG. 3 illustrates a further embodiment of an inventive wound dressing. This wound dressing differs from the dressing illustrated in FIGS. 1 and 2, insomuch that the carrier material 7 is comprised of a plastic film having perforations 8 provided in the bottoms of cup-shaped projections in the plastic film. Such plastic films are known to the art and are sometimes used as casing sheets for diapers and similar absorbent articles. In addition to the surface area for adhesion between silicone gel and the plastic sheet being greater than the surface area of the embodiment of the inventive dressing described with reference to FIGS. 1 and 2, the cupped shape of the projections 9 also reduces the risk of non-cured silicone mixture running down into the perforations 8 during the process of manufacture. This obviates the need, or at least greatly reduces the need, of blowing hot air onto the carrier material before passing the carrier material and its silicone coating into a curing oven.

When practicing the method of manufacture taught by EP-C 0,261,167, it is necessary to transport that part of the material to be embraced by silicone gel in an unsupported fashion. When practicing the present invention, on the other hand, the carrier material can be transported on an air-permeable conveyor, provided that the holes in the conveyor are sufficiently large to ensure that the delivery of air onto the underside of the carrier material will not be disturbed thereby.

Thus, when practicing the inventive method, the carrier material can be transported at a higher speed than in the case of the aforesaid known method and the conveyor path can be guided much more easily than in the earlier known case.

In the case of the described embodiment of the inventive method of manufacture, the carrier material is comprised of a continuous web which is moved past the nozzles and the air-blowing units. Although this embodiment is to be preferred, it lies within the scope of the invention to hold the carrier material stationary and to move nozzles and air blowers in relation to said material.

As will be understood, modifications can be made to the described embodiment of the inventive arrangement for manufacturing an inventive wound dressing within the scope of the present invention. For instance, the air-blowing units 4 and 5 may be combined to form a single unit and may be supplied with air under pressure from one and the same source, for instance from the same blower fan, which may be beneficial in obtaining an homogenous air flow in the longitudinal direction. The hot air section of such a unit will include an appropriate heat source, such as electrical heating wires or filaments. Furthermore, at least the hot air-blowing unit will be conveniently accommodated in a housing which will enable the heat content of the hot air to be better utilized for delivering heat to the silicone mixture coated on the carrier material from above.

This invention thus provides a simple and effective method of manufacturing a wound dressing having a layer of hydrophobic silicone gel which is intended to lie against the wound or sore, and a layer of carrier material which when the dressing is worn faces outwardly and which is not sticky and will not adhere to clothing and the like. As in the case of the aforesaid known dressing, the layer of hydrophobic silicone gel which lies against the wound or sore is soft and adheres to dry skin, and the inventive dressing will therewith facilitate healing of the wound in the same beneficial fashion as the known dressing. According to the present invention, the silicone gel is comprised of chemically cross-linked, two-component additioncuring silicone gel.

The carrier material will preferably have 0.5–200 perforations per $cm^2$ and the perforations will preferably have a diameter of 0.1–2 mm. When practicing the inventive method of manufacture, good homogeneity is obtained with regard to the size of the perforations in the gel layer, therewith enabling an inventive dressing to be constructed for smaller-sized perforations than the aforesaid known dressing, without the risk of the perforations being clogged or blocked by silicone gel in the manufacturing process.

The silicone gels used in accordance with the present invention are soft and will adhere to dry skin but not to the wound or sore. This extremely low or weak adhesion to wounds as compared with other so-called non-adhesive dressings is achieved because the silicone gel has an extremely low surface tension and a surface chemistry which forms other types of adhesion forces on the wound surface than other polymeric and metallic materials used in such dressings, wherewith the strength at which the silicone gel adheres to the wound surface is weaker than practically all of these polymers and metallic materials. The silicone gel is also form-stable, i.e. it retains its original form when handled normally. Thus, the silicone gel undergoes no plastic deformations when the dressing lies against the wound or when the dressing is removed or when protective covering strips are peeled from the gel surface, etc. The gel surface obtained when practicing the inventive method is also very smooth and even, which also contributes to the poor adhesion of the gel layer to the wound surface. The majority of other types of so-called non-adhering dressings have a larger available surface area than the inventive dressing, as seen both macroscopically and microscopically which results in stronger adhesion to the wound and to the dried wound fluid.

The strength at which the silicone gels used with the inventive dressing adhere to dry skin is considerably lower than the adhesive strength of those adhesives used with conventional self-adhesive tapes used to secure wound dressings, or those adhesives used with conventional self-adhesive wound dressings. Thus, the skin will not be damaged or injured by the adhesive silicone gel when removing the inventive dressing. One method of measuring this adhesive strength is to stick 25 mm wide strips of an inventive dressing onto dry skin and to allow a weight attached to one end of the strip to draw the dressing gravitationally from the skin at an angle of 160° thereto. The weight which will draw, or peel, the dressing from the skin at a speed of 1 mm/s can be determined with the aid of this test. The adherency measured in accordance with this test shall lie within the range of 5–200 g, preferably within the range of 20–60 g, in order to provide satisfactory adhesion and dressing peelability.

The hardness of the silicone gel is measured by means of a method in which a round steel rod having a flat end and a diameter of 9.2 mm is pressed into the gel to a depth of 5 mm. The force required to achieve this depth of penetration is measured during the process. A silicone gel suitable for use in an inventive dressing will have a hardness which lies in the range of 0.5–10N An optimum hardness value is 2N.

The penetrability of a silicone gel is measured with the aid of a method in which a conical test body is allowed to sink gravitationally into the silicone gel. The number of mm through which the test body has sunk over a time period of 5 seconds constitutes the penetration value. In this test, there is used a cone obtained from Sommer & Runge AG and designated Petrotest Sommer & Runge 18-036.1, which is filled with glass spheres to a weight of 62.5 g. A silicone gel suitable for use in an inventive dressing will have a penetrability which lies within the range of 5–20 mm. An optimum penetrability value is 9 mm.

The tensile strength of a silicone gel is determined with the aid of a method in which a gel test strip is fastened vertically between two clamps, of which one can be moved at a constant speed. The strip is stretched to a point at which it fractures and the maximum fracturing force is recorded. A silicone gel suitable for use with an inventive dressing will have a tensile strength within the range of 1–8N/10 mm in the case of a 3 mm thick strip, and will preferably be 4N/10 mm.

In addition to adhering to dry skin, the silicone gel will also adhere to other dry surfaces, and a good estimate of the adherence of the gel to dry skin can be obtained by measuring the force with which the gel adheres to a highly polished steel plate. The adherence of the silicone gel to a steel surface is determined by means of a method in which a test strip of silicone gel is applied to a steel plate and the strip then drawn or peeled from the plate with the withdrawn part of the strip being held at an angle of 90° thereto. The force required to withdraw or peel the strip from the plate is recorded. A silicone gel suitable for use with an inventive dressing will have an adhesive force within the range of 0.5–10N/50 mm, preferably 2N/50 mm, as measured in accordance with this method.

I claim:

1. A method of manufacturing wound dressings, which comprises:

applying a coating of curable silicone mixture to an upper surface of a perforated carrier material;

blowing cold air onto an underside of the coated carrier material so that the silicone mixture is blown away from the perforations in the carrier material so as to form through penetrating perforations and prevent clogging of the perforations in the carrier material; and applying heat to the silicone mixture until it has cured.

2. A method according to claim 1, further comprising blowing hot air onto the underside of the coated carrier material after blowing cold air thereonto until the silicone mixture has cured.

3. A method according to claim 2, further comprising interrupting the delivery of hot air onto the underside of said coated material before the silicone mixture has completely cured, and terminating the curing process in an oven.

4. A method according to claim 1, further comprising taking the carrier material from a storage reel and passing the material past a station in which the upper surface of the material is coated with said silicone mixture while, at the same time, delivering a flow of cold air to the underside of said material essentially perpendicularly to said underside, and then passing the carrier material coated with said silicone mixture past a device which functions to blow hot air onto the underside of said carrier material.

5. Apparatus for manufacturing a wound dressing having a perforated carrier material and a layer of hydrophobic silicone gel, said apparatus comprising:

means for coating an upper surface of the carrier material with a mixture of components which when cured form a silicone gel;

an air-blowing unit for blowing cold air onto an underside of the carrier material, said air blowing unit being placed opposite the coating means; and means for delivering heat to the mixture of components applied to the upper surface of the carrier material.

6. Apparatus according to claim 5, wherein the means for delivering heat is a hot-air blowing unit.

7. A wound dressing comprising a perforated carrier material and a layer of hydrophobic silicone gel which lies against a wound surface when the dressing is worn, said carrier material being impervious to air and fluid, or only slightly permeable to air and fluid in the parts thereof lying between perforations; said carrier material being coated with silicone gel on only one side thereof, and said layer of silicone gel having through penetrating perforations coinciding with the perforations in the carrier material.

8. A wound dressing according to claim 7, wherein the carrier material is comprised of a soft plastic film.

9. A wound dressing according to claim 8, wherein the plastic film is microporous.

10. A wound dressing according to claim 7, wherein the carrier material is coated with a silicone primer.

11. A wound dressing according to claim 7, wherein the carrier material is comprised of a two-ply material, including a plastic layer and a layer of fibre material.

12. A method according to claim 1, wherein the carrier material has from about 0.5 to about 200 perforations per cm$^2$, said perforations having a diameter ranging from about 0.1 to about 2 mm.

13. Apparatus according to claim 5, wherein the carrier material has from about 0.5 to about 200 perforations per cm$^2$, said perforations having a diameter ranging from about 0.1 to about 2 mm.

14. A wound dressing according to claim 7, wherein the carrier material has from about 0.5 to about 200 perforations per cm$^2$, said perforations having a diameter ranging from about 0.1 to about 2 mm.

* * * * *

US005635201C1

(12) EX PARTE REEXAMINATION CERTIFICATE (8025th)
United States Patent
Fabo

(10) Number: US 5,635,201 C1
(45) Certificate Issued: Feb. 15, 2011

(54) METHOD AND AN ARRANGEMENT FOR MANUFACTURING WOUND DRESSINGS, AND A WOUND DRESSING MANUFACTURED IN ACCORDANCE WITH THE METHOD

(75) Inventor: Tomas Fabo, Mölnlycke (SE)

(73) Assignee: Molnlycke Health Care AB, Gothenburg (SE)

Reexamination Request:
No. 90/009,458, Apr. 27, 2009

Reexamination Certificate for:
Patent No.: 5,635,201
Issued: Jun. 3, 1997
Appl. No.: 08/302,875
Filed: Sep. 14, 1994

(22) PCT Filed: Mar. 30, 1993

(86) PCT No.: PCT/SE93/00270
§ 371 (c)(1),
(2), (4) Date: Sep. 14, 1994

(87) PCT Pub. No.: WO93/19709
PCT Pub. Date: Oct. 14, 1993

(30) Foreign Application Priority Data

Mar. 30, 1992 (SE) .............................. 9200983

(51) Int. Cl.
A61F 13/00 (2006.01)
A61F 13/02 (2006.01)

(52) U.S. Cl. ........................ 424/443; 424/449; 427/2.31; 427/348; 602/47

(58) Field of Classification Search ........................ None
See application file for complete search history.

(56) References Cited

U.S. PATENT DOCUMENTS

| | | | |
|---|---|---|---|
| 2,764,976 A | 10/1956 | Skiles, Jr. et al. | 602/51 |
| 3,006,338 A | 10/1961 | Davies | 602/43 |
| 3,020,260 A | 2/1962 | Nelson | 528/15 |
| 3,042,549 A | 7/1962 | Arnold | 524/733 |
| 3,050,490 A | 8/1962 | Nitzsche et al. | 524/404 |
| 3,050,491 A | 8/1962 | Nitzsche et al. | 524/588 |
| 3,070,567 A | 12/1962 | Nitzsche et al. | 524/108 |
| 3,113,568 A | 12/1963 | Robins | 602/46 |
| 3,146,799 A | 9/1964 | Fekete | 428/34.2 |
| 3,285,245 A | 11/1966 | Eldredge et al. | 602/52 |
| 3,439,676 A | 4/1969 | Burda | 604/290 |
| 3,671,483 A | 6/1972 | Young | 106/285 |
| 3,697,473 A | 10/1972 | Polmanteer et al. | 524/862 |
| 3,767,784 A | 10/1973 | Gluck | 424/445 |
| 3,790,433 A | 2/1974 | Baron | 428/138 |
| 3,888,247 A | 6/1975 | Stenvall | 602/59 |
| 4,034,751 A | 7/1977 | Hung | 602/52 |
| 4,051,848 A | 10/1977 | Levine | 604/304 |
| 4,175,557 A | 11/1979 | Hung | 602/42 |
| 4,178,336 A | 12/1979 | Snowden | 264/8 |
| 4,233,969 A | 11/1980 | Lock et al. | 602/46 |
| 4,243,656 A | 1/1981 | Walliczek | 424/78.06 |
| 4,304,286 A | 12/1981 | Waldron | 164/4.1 |
| 4,307,717 A | 12/1981 | Hymes et al. | 604/304 |
| 4,311,760 A | 1/1982 | Kalinowski et al. | 428/391 |

(Continued)

FOREIGN PATENT DOCUMENTS

| | | |
|---|---|---|
| CA | 1 193 966 A | 9/1985 |
| CA | 2 132 984 C | 10/1993 |
| CA | 1 329 082 C | 5/1994 |
| CA | 2 132 983 C | 8/2004 |
| CA | 2 633 169 A1 | 6/2007 |
| DE | 2 132 498 | 6/1972 |
| DE | 100 08 827 | 9/2001 |
| EP | 0 099 675 A1 | 2/1984 |
| EP | 0 100 148 | 2/1984 |
| EP | 0 251 810 A2 | 1/1988 |
| EP | 0251810 | 1/1988 |
| EP | 0 194 881 B1 | 1/1991 |
| EP | 0 261 167 B1 | 1/1992 |
| EP | 0 251 810 B1 | 10/1992 |
| EP | 0 633 757 B1 | 1/1995 |
| EP | 0 633 758 B1 | 1/1995 |
| EP | 0 251 810 B2 | 9/2001 |
| EP | 1 175 527 B1 | 1/2002 |
| EP | 1 082 147 B1 | 8/2004 |
| EP | 1 528 133 | 5/2005 |

(Continued)

OTHER PUBLICATIONS

Quinn, "The Application of Silicone Gel for Treatment of Hypertrophic Scars and Burn Wounds, and Consideration of the 'Ideal' Burn Dressing," Doctoral Thesis, Bioengineering Unit, University of Strathclyde, Glasgow, Scotland (Apr. 1, 1986).

Malone, "Wound dressing adherence: a clinical comparative study," Archives of Emergency Medicine, vol. 4, pp. 101–105 (1987).

Sirvio et al., "The Effect of Gas Permeability of Film Dressings on Wound Environment and Healing," J Invest Dermatol 93:528–531, 1989.

(Continued)

Primary Examiner—Gary L Kunz

(57) ABSTRACT

A method and apparatus for manufacturing a wound dressing, and a wound dressing produced thereby. The upper surface of a perforated carrier material (2) is coated with a curable silicone mixture (3) and cold air is blown onto the underside of the coated carrier material. Heat is then applied to the silicone mixture until it has cured to a silicone gel.

At the time of issuance and publication of this certificate, the patent remains subject to pending reexamination control number 90/011,259 filed Sep. 30, 2010. The claim content of the patent may be subsequently revised if a reexamination certificate issues from the reexamination proceeding.

U.S. PATENT DOCUMENTS

| | | | | |
|---|---|---|---|---|
| 4,312,693 | A | 1/1982 | Salensky et al. | 156/272.2 |
| 4,404,296 | A | 9/1983 | Schäpel | 523/105 |
| 4,456,642 | A | 6/1984 | Burgdörfer et al. | 428/68 |
| 4,499,896 | A | 2/1985 | Heinecke | 602/47 |
| 4,513,115 | A | 4/1985 | Beers | 524/731 |
| 4,528,353 | A | 7/1985 | Lucas et al. | 528/21 |
| 4,541,426 | A | 9/1985 | Webster | 602/47 |
| 4,572,814 | A | 2/1986 | Naylor et al. | 264/46.4 |
| 4,608,044 | A | 8/1986 | Nordqvist et al. | 604/290 |
| 4,624,900 | A | 11/1986 | Fau | 428/447 |
| 4,661,099 | A | 4/1987 | Von Bittera et al. | 604/290 |
| 4,664,662 | A | 5/1987 | Webster | 602/47 |
| 4,684,538 | A | 8/1987 | Klemarczyk | 427/515 |
| 4,684,557 | A | 8/1987 | Pennace et al. | 428/40.9 |
| 4,690,683 | A | 9/1987 | Chien et al. | 424/448 |
| 4,726,976 | A | 2/1988 | Karami et al. | 428/137 |
| 4,727,868 | A | 3/1988 | Szycher et al. | 602/43 |
| 4,747,895 | A | 5/1988 | Wallerstein et al. | 156/73.3 |
| 4,753,231 | A | 6/1988 | Lang et al. | 602/47 |
| 4,781,962 | A | 11/1988 | Zamarripa et al. | 428/138 |
| 4,838,253 | A | 6/1989 | Brassington et al. | 602/48 |
| 4,841,962 | A | 6/1989 | Berg et al. | 602/50 |
| 4,860,737 | A | 8/1989 | Lang et al. | 602/43 |
| 4,921,704 | A | 5/1990 | Fabo | 424/446 |
| 4,928,681 | A | 5/1990 | Langston et al. | 602/58 |
| 4,935,087 | A | 6/1990 | Gilman | 156/251 |
| 4,950,148 | A | 8/1990 | Nakanishi | 425/224 |
| 4,957,795 | A | 9/1990 | Riedel | 428/74 |
| 4,991,574 | A | 2/1991 | Pocknell | 602/48 |
| 4,995,382 | A | 2/1991 | Lang et al. | 602/55 |
| 4,995,930 | A | 2/1991 | Merz et al. | 156/209 |
| 5,004,643 | A | 4/1991 | Caldwell | 442/82 |
| 5,052,381 | A | 10/1991 | Gilbert et al. | 602/52 |
| 5,153,040 | A | 10/1992 | Faasse, Jr. | 428/41.5 |
| 5,167,613 | A | 12/1992 | Karami et al. | 602/42 |
| 5,209,965 | A | 5/1993 | Caldwell | 442/81 |
| 5,219,325 | A | 6/1993 | Hennink et al. | 602/41 |
| 5,258,211 | A | 11/1993 | Momii et al. | 428/35.2 |
| 5,312,690 | A | 5/1994 | Fukuda et al. | 428/447 |
| 5,322,729 | A | 6/1994 | Heeter et al. | 428/306.6 |
| 5,340,363 | A | 8/1994 | Fabo | 604/304 |
| 5,352,508 | A | 10/1994 | Cheong | 442/43 |
| 5,418,051 | A | 5/1995 | Caldwell | 442/61 |
| 5,540,922 | A | 7/1996 | Fabo | 424/402 |
| 5,674,211 | A | 10/1997 | Ekdahl | 604/383 |
| 5,863,625 | A | 1/1999 | Chiou | 428/36.1 |
| 5,891,076 | A | 4/1999 | Fabo | 602/52 |
| 6,051,747 | A | 4/2000 | Lindqvist et al. | 602/46 |
| 6,197,845 | B1 | 3/2001 | Janssen et al. | 523/111 |
| 6,479,724 | B1 | 11/2002 | Areskoug et al. | 602/41 |
| 6,846,508 | B1 | 1/2005 | Colas et al. | 427/2.31 |
| 7,220,889 | B2 | 5/2007 | Sigurjonsson et al. | 602/58 |
| 2002/0177669 | A1 | 11/2002 | Jenny et al. | 525/332.8 |
| 2007/0042108 | A1 | 2/2007 | Gantner et al. | 427/2.1 |
| 2009/0211693 | A1 | 8/2009 | Zawadzki et al. | 156/73.3 |

FOREIGN PATENT DOCUMENTS

| | | |
|---|---|---|
| FI | 87519 C | 1/1993 |
| FR | 2 285 112 | 4/1976 |
| GB | 713 838 | 8/1954 |
| GB | 713838 | 8/1954 |
| GB | 830 177 | 3/1960 |
| GB | 830177 | 3/1960 |
| GB | 898826 | 6/1962 |
| GB | 1 328 890 | 9/1973 |
| GB | 2 070 631 A | 9/1981 |
| GB | 2 313 338 A | 11/1997 |
| JP | 62-53651 A | 3/1987 |
| JP | 63-502804 A | 10/1988 |
| JP | 2 525 215 B2 | 8/1996 |
| JP | 3 677 282 B2 | 7/2005 |
| SE | 455 466 | 7/1988 |
| SE | 500 972 C2 | 10/1994 |
| SE | 500 973 C2 | 10/1994 |
| SE | 530 256 C2 | 4/2008 |
| WO | WO 87/05206 A1 | 9/1987 |
| WO | WO 91/01706 | 2/1991 |
| WO | WO 91/01706 A1 | 2/1991 |
| WO | WO 93/19709 A1 | 10/1993 |
| WO | WO 93/19710 A1 | 10/1993 |
| WO | WO 96/14191 A1 | 5/1996 |
| WO | WO 99/61077 | 12/1999 |
| WO | WO 99/61078 | 12/1999 |
| WO | WO 2007/069990 A1 | 6/2007 |

OTHER PUBLICATIONS

Quinn, Karen J., Thesis submitted for the degree of Doctor of Philosophy, "The Application of Silicone Gel for Treatment of Hypertrophic Scars and Burn Wounds, and Consideration of the 'Ideal' Burn Dressing," Bioengineering Unit, University of Strathclyde, Glasgow, Scotland, Apr. 1, 1986.

Malone, W.D., "Wound Dressing Adherence: A Clinical Comparitive Study," *Archives of Emergency Medicine*, 1987, vol. 4, pp. 101–105.

U.S. Appl. No. 06/396,754 to Lang et al. (as incorporated by reference into #2 above).

English translation of German Nullity Action and Annexes filed by Smith & Nephew GmbH against the German part DE 693 11 101 of the European Patent EP 0 633 757, with respect of claims 6–10.

Billmeyer, Jr., Textbook of Polymer Science 448–451 ($3^{rd}$ ed. 1984).

Perkins, et al., "Silicone Gel: A New Treatment for Burn Scars and Contractures," *Burns*, 9(3), 201–204 (1982).

Fortess, "Silicone Resins in Textiles," *Industrial and Engineering Chemistry*, vol. 46, No. 11, 2325–2331 (1954).

English Translation of Prosecution History Documents, Apr. 3, 2009.

English Translation of Application and Filing Receipt, Jun. 4, 2008.

English Translation of Transmittal Letter, Jul. 15, 2008.

English Translation of Specification, Jul. 15, 2008.

English Transaltion of Claims, Jul. 15, 2008.

English Translation of Abstract, Jul. 15, 2008.

English Translation of Official Filing Receipt, Jul. 22, 2008.

English Translation of Amended Claims, Jul. 15, 2008 or later.

English Translation of Notification of the Positive Results of the Formal Examination, Sep. 2, 2008.

English Translation of Application as filed Nov. 6, 1987.

English Translation of DKPTO Office Action, Aug. 17, 1995.

English Translation of Letter from DKPTO re abandonment, Feb. 28, 1996.

Reply filed by Mölnlycke Health Care AB in response to German Nullity Action and Annexes filed by Smith & Nephew GmbH, Jan. 7, 2010.

Report on the Wound Dressing as Described in European Patent 0 251 810, filed as Exhibit 1 to the Jan. 7, 2010 Reply, Nov. 23, 2009.

English Translation of the Report on the Wound Dressing as Described in European Patent 0 251 810, which was filed as Exhibit 1 to the Jan. 7, 2010 Reply, Nov. 23, 2009.

Packaging information for Mölnlycke Health Care AB's Mepitel® product, filed as Exhibit 2 to the Jan. 7, 2010 Reply, Jan. 7, 2010.
English Translation of Examination Document, May 31, 2006.
English Translation of Examination Document, Feb. 28, 2007.
English Translation of Search Report and Office Action, Nov. 20, 1992.
English Translation of Response to Office Action, May 11, 1993.
English Translation of Claims field with Response, May 11, 1993.
English Translation of Replacement p. 2 filed with Response, May 11, 1993.
English Translation of Notice of Allowance, Jun. 29, 1994.
English Translation of Examination Document, Nov. 20, 1992.
Counterpart Response to Mölnlycke Brief in Response to Brief of the Counterpart, Feb. 3, 2010.
English Translation of Counterpart Response to Mölnlycke Brief in Response to Brief of the Counterpart, Feb. 3, 2010.
Exhibit 5 of Feb. 3, 2010 Counterpart Response—German Translation of English Patent No. GB 713,838, Aug. 18, 1954.
Exhibit 6 of Feb. 3, 2010 Counterpart Response—German Translation of Order Granting Request for *Ex Parte* Reexamination (Control U.S. Appl. No. 90/009,458), Jun. 26, 2009.
Exhibit 7 of Feb. 3, 2010 Counterpart Response—Materials Testing Laboratory Test Report on Measurement of Air and Liquid Permeability of Counterpart's Carrier Material, Feb. 3, 2010.
German Translation of Exhibit 7 of Feb. 3, 2010 Counterpart Response—Materials Testing Laboratory Test Report on Measurement of Air and Liquid Permeability of Counterpart's Carrier Material, Feb. 3, 2010.
Exhibit 8 of Feb. 3, 2010 Counterpart Response—Laboratory Report of Water Vapor and Liquid Permeability of Counterpart's Carrier Material and Other Carrier Materials, entitled "Physical analyses of permeable and non–permeable materials", Jan. 2010.
German Translation of Exhibit 8 of Feb. 3, 2010 Counterpart Response—Internal Laboratory Report Comparing Water Vapor and Liquid Permeability of Counterpart's Carrier Material with that of Other Carrier Materials, entitled "Physical analyses of permeable and non–permeable materials", Jan. 2010.
Exhibit 9 of Feb. 3, 2010 Counterpart Response—European Standard for "Test methods for primary wound dressings—Part 2: Moisture vapour transmission rate of permeable film dressings", Oct. 1999.
Exhibit 10 of Feb. 3, 2010 Counterpart Response—*British Pharmacopoeia*, Appendix XX, p. A222–A224 (1993) (describing water vapor permeability), Jun. 1993.
German Translation of Exhibit 10 of Feb. 3, 2010 Counterpart Response—*British Pharmacopoeia*, Appendix XX, p. A222–A224 (1993) (describing water vapor permeability), Jun. 1993.
Exhibit 11 of Feb. 3, 2010 Counterpart Response—Summary of Counterpart Testing of Methods for Achieving One–Sided Coating of Perforated Polyurethane Film, Feb. 3, 2010.
German Translation of Exhibit 11 of Feb. 3, 2010 Counterpart Response—Summary of Counterpart Testing of Methods for Achieving One–Sided Coating of Perforated Polyurethane Film, Feb. 3, 2010.
Published Minutes of Oral Proceedings before the Regional Court—Landgericht—Düsseldorf, Feb. 23, 2010.
Supplemental Counterpart Response to Mölnlycke Brief in Response to Brief of the Counterpart (including Exhibit), Feb. 26, 2010.
Exhibit 12 of Feb. 26, 2010 Supplemental Counterpart Response—Difinition of "Fluid" from German Wikipedia website: http://de.wikipedia.org/wiki/Fluid, Feb. 26, 2010.
Supplemental Counterpart Response to Mölnlycke Brief in Response to Brief of the Counterpart (including Exhibits), Mar. 3, 2010.
Exhibit 13 of Mar. 3, 2010 Supplemental Counterpart Response—Published Decision by German Civil Court, Feb. 15, 2005.
Judgment of Regional Court—Landgericht—Düsseldorf, Mar. 16, 2010.
English Translation of Judgement of Regional Court—Landgericht—Düsseldorf, Mar. 16, 2010.
Correspondence related to execution and recordation of assignment from inventors to Mölnlycke Health Care AB, Mar. 26, 2010.
English Translation of Application, Jun. 13, 2008.
Direction to Request Examination, Nov. 24, 2009.
Request for Examination, Apr. 29, 2010.
English Translation of Reply filed by Mölnlycke Health Care AB in Response to German Nullity Action and Annexes filed by Smith & Nephew GmbH, Jan. 7, 2010.
International–Type Search Report (English), May 31, 2006.
Office Action (English), Oct. 14, 2003.
Argument (English), Jan. 14, 2004.
Office Action (English), Jul. 6, 2004.
Argument (English), Dec. 15, 2004.
Amendment (English), Dec. 15, 2004.
Notice of Allowance (English), Apr. 12, 2005.
International Search Report (English), Jul. 1, 1993.
International Preliminary Examination Report (English), Jul. 14, 1994.
International–Type Search Report (English), Nov. 20, 1992.
Counterpart Request for Dismissal (German), Feb. 4, 2009.
Minutes of Oral Hearing (German), Feb. 17, 2009.
Mölnlycke Brief in Support of Complaint (German), Jun. 24, 2009.
English Translation of Court Order Regarding Hearing Date, Sep. 28, 2009.
English Translation of Mölnlycke Request for Extension of Time to file Brief in Response to Brief of the Counterpart, Nov. 6, 2009.
English Translation of Mölnlycke Brief in Response to Brief of the Counterpart, Dec. 7, 2009.
English Translation of Published Minutes of Oral Proceedings before the Regional Court–Landgericht–Düsseldorf, Feb. 23, 2010.
English Translation of Supplemental Counterpart Response to Mölnlycke Brief in Response to Brief of the Counterpart (including Exhibit), Feb. 26, 2010.
English Translation of Exhibit 12 of Feb. 26, 2010 Supplemental Counterpart Response—Definition of "Fluid" from German Wikipedia website: http://de.wikipedia.org/wiki/Fluid, Feb. 26, 2010.

English Translation of Supplemental Counterpart Response to Mölnlycke Brief in Response to Brief of the Counterpart (including Exhibits), Mar. 3, 2010.
English Translation of Exhibit 13 of Mar. 3, 2010 Supplemental Counterpart Response—Published Decision by German Civil Court, Feb. 15, 2005.
Exhibit K1 of Mölnlycke Pleadings—EP 0 633 757 B1 (English), Jan. 18, 1995.
Exhibit K2 of Mölnlycke Pleadings—DE 693 11 101 T2 (German), Jan. 18, 1995.
Exhibit K3 of Mölnlycke Pleadings—German Patent and Trademark Office Register Information regarding DE 693 11 101 T2 (English and German), Dec. 19, 2008.
Exhibit K4 of Mölnlycke Pleadings—Mölnlycke Website Pages (English), Dec. 19, 2008.
Exhibit K5 of Mölnlycke Pleadings—Smith & Nephew Website Pages (English and German), Dec. 19, 2008.
Exhibit K6 of Mölnlycke Pleadings—Packaging of Smith & Nephew Allevyn® Gentle Border wound dressing product (English and German), Dec. 19, 2008.
Exhibit K7 of Mölnlycke Pleadings—Smith & Nephew Medical Products Catalog (English and German), Sep. 2008.
Exhibit K8 of Mölnlycke Pleadings—WO 87/05206 (English), Sep. 11, 1987.
Exhibit K9 of Mölnlycke Pleadings—List of Features of Claim 6 of EP 0 633 757 (English and German), Dec. 19, 2008.
Exhibit K10 of Mölnlycke Pleadings—Photograph of cross-section of Smith & Nephew Allevyn® Gentle Border wound dressing product, Dec. 19, 2008.
Exhibit K11 of Dec. 7, 2009 Mölnlycke Response Brief—Report on the Wound Dressing as Described in European Patent 0 251 810, conducted by Giles Dillingham, Ph. D.; Curriculum Vitae of Dr. Dillingham, Nov. 23, 2009.
Exhibit 12 of Jun. 24, 2009 Mölnlycke Brief in Support of Complaint—Allevyn® Gentle Border product packaging and instruction manual, Jun. 24, 2009.
Exhibit 1 of Counterpart Pleadings—German Nullity Action and Annexes filed by Smith & Nephew GmbH against the German part DE 693 11 101 of the European Patent EP 0 633 757 (German), May 6, 2009.
Exhibit 2 of Counterpart Pleadings—List of Features of Claim 6 of EP 0 261 167 (English), Jul. 31, 2009.
Exhibit 3 of Counterpart Pleadings—Patent No. GB 713,838 (English), Aug. 18, 1954.
Exhibit 4 of Counterpart Pleadings—Patent No. EP 0 251 810 (English), Jan. 7, 1988.
Exhibit 5 of Counterpart Pleadings—U.S. Patent No. 4,921,704, May 1, 1990.
Exhibit 6 of Counterpart Pleadings—Order Granting Request for Ex Parte Reexamination (U.S. Control No. 90/009,458) (English), Jun. 26, 2009.
Counterpart Appellate Brief (German), May 5, 2010.
Mölnlycke Appellate Requests and Objection to Counterpart Application (German), May 31, 2010.
Mölnlycke Appellate Requests and Objection to Counterpart Application (English translation), May 31, 2010.
Exhibit 15-1 of Counterpart Appellate Brief—International Patent Publication No. WO 91/01706 (English), Feb. 21, 1991.
Exhibit 15-2 of Counterpart Appellate Brief—U.S. Patent No. 4,935,087, Jun. 19, 1990.
Exhibit 15-3 of Counterpart Appellate Brief—U.S. Patent No. 4,995,382, Feb. 26, 1991.
Exhibit 15-4 of Counterpart Appellate Brief—Patent No. GB 830,177, Mar. 9, 1960.
Exhibit 16-1 of Counterpart Appellate Brief—Quinn (thesis)—"The Application of Silicone Gel for Treatment of Hypertrophic Scars and Burn Wounds, and Consideration of the 'Ideal' Burn Dressing" (English), Apr. 1, 1986.
Exhibit 16-2 of Counterpart Appellate Brief—Malone, "Wound dressing adherence: a clinical comparitive study" (English), 1987.
Exhibit 17-1 of Counterpart Appellate Brief—German Supreme Court decision (German), Sep. 18, 2006.
Exhibit 17-2 of Counterpart Appellate Brief—German Supreme Court decision (German), Jul. 10, 2008.
Exhibit 18 of Counterpart Appellate Brief—First Office Action from Ex Parte Re–examination (U.S. Control No. 90/009,458), Mar. 30, 2010.
Exhibit 19 of Counterpart Appellate Brief—Bank Guarantee of Mölnlycke Health Care AB (German); Notice of Service of Bank Guarantee by Bailiff (English), Apr. 27, 2010 and May 3, 2010.
Scanned images of inner and outer packaging of various Mölnlycke Health Care wound dressing products.
Scanned images of inner and outer packaging of various wound dressing products that are produced by competitors of Mölnlycke Health Care.
English excerpts of instruction manuals provided with various Mölnlycke Health Care wound dressing products.
Instruction manual for Smith & Nephew Allevyn® Gentle Border wound dressing product.
Copies of promotional materials associated with various Mölnlycke Health Care wound dressing products.
Copies of promotional materials associated with various Smith & Nephew wound dressing products.
Krasner, D., and McNeil, M., "Six Strategies for Minimizing Wound Pain: Translating the Results from a US Pain Survey into Clinical Practice," E.C.P.N Mar./Apr. 2008, pp. 16–21.
Caine, S. (ed.), "Pain at wound dressing changes," Position Document, European Wound Mangement Association, Medical Education Partnership Ltd. (2002).
Woo et al., "A Randomized Crossover Investigation of Pain at Dressing Change Comparing 2 Foam Dressings," Advances in Skin & Wound Care, vol. 22, No. 7, pp. 304–310 (Jul. 2009).
Davies et al., "Evidence Review: The clinical benefits of Safetac® technology in wound care," Safetac Evidence Review, MA Healthcare Ltd., London (Nov. 2008).
"When Wound Care Hurts: The Importance of Addressing the Pain," Ostomy Wound Management, vol. 51, No. 11A (Suppl) (Nov. 2005).
White, R., "Evidence for atraumatic soft silicone wound dressing use," Wounds UK, vol. 1, No. 3, pp. 1–6 (Nov. 2005).
SMTL Dressings Datacard, "Silastic foam" (classified as Dressing Cavity Wound and Silicone Foam BP, manufactured by Dow Corning), available at: http://www.dressings.org/Dressings/silastfm.html (revised Dec. 16, 1997).
"Viscosity," from Wikipedia Free Online Encyclopedia, available at http://en:wikipedia.org/wiki/Viscosity (Jun. 22, 2010).
Smith & Nephew Annual Report (2008).
Silopren® RTV 2K Gel TP 3293 Kit Product Description, GB Bayer Silicones.
Silopren® RTV 2K Gel TP 3293 Safety Data Sheet, Momentive Performance Materials (May 5, 2009).

Dow Corning® Q7–2218 Silicone Gel System Product Information (Jul. 1997).

Kessler, D., "The Basis of the FDA's Decision on Breast Implants," N. Eng. J. Med., 326(25):1713–15 (Jun. 18, 1992).

"Adhesive," from Wikipedia Free Online Encyclopedia, available at http://en.wikipedia.org/wiki/Adhesive (Jun. 16, 2010).

"Gel," from Wikipedia Free Online Encyclopedia, available at http://en.wikipedia.org/wiki/Gel (Jun. 7, 2010).

"Pressure–sensitive adhesive," from Wikipedia Free Online Encyclopedia, available at http://en.wikipedia.org/wiki/Pressure–sensitive_adhesive (May 7, 2010).

"Silicone," from Wikipedia Free Online Encyclopedia, available at http://en.wikipedia.org/wiki/Silicone (Jun. 16, 2010).

"Silicone rubber," from Wikipedia Free Online Encyclopedia, available at http://en.wikipedia.org/wiki/Silicone_rubber (Apr. 16, 2010).

Mölnlycke Health Care brochure, "Clinical Education Resource Center" (May 2009).

Mölnlycke Health Care, Wound Care Product Guide (Jan. 2010).

Mölnlycke Health Care, Wound Care Dressing Selection Guides (Jan. 2010).

Mölnlycke Health Care, Dressing Selection Guide by Wound Condition (Sep. 2008).

Mölnlycke Health Care, Newborn and NICU Wound Dressing Selection Guide (Aug. 2009).

Mölnlycke Health Care, Hospice/Palliative Care Wound Dressing Selection Guide (Sep. 2008).

Mölnlycke Health Care, Skin Tear Dressing Selection Guide (Jan. 2010).

Mölnlycke Health Care, Emergency Department Dressing Selection Guide (Feb. 2009).

Mölnlycke Health Care, Burn Care Dressing Selection Guide (Mar. 2009).

Mölnlycke Health Care, Wound Dressing Selection Guide for Surgical Procedures (Feb. 2010).

Mölnlycke Health Care brochure, "The range that covers your needs" (Aug. 2008).

Mölnlycke Health Care, Mepilex® Product Application Guide (Aug. 2008), Mepilex® Ag Product Application Guide (Aug. 2009), and Mepilex Border Product Application Guide (Jan. 2010).

Mölnlycke Health Care, Mepitel Application Guide (Nov. 2009).

Mölnlycke Health Care, Newborn Product Application Guide (May 2009).

Mölnlycke Health Care, Tubigrip® Product Application Guide (Jan. 2010).

Mölnlycke Health Care brochure, "Mepitel®: The Soft Silicone Wound Contact Layer" (2006).

Weir et al., "The Pressure's On!: Getting it Right on Admission," Mölnlycke Health Care (Jan. 2009).

Mölnlycke Health Care, "The Pressure's On!: Getting it Right on Assessment—A Guide to Pressure Ulcer Staging" (May 2009).

Mölnlycke Health Care brochure, "Foam Dressings with Safetac® Technology: Building a standardized Formulary for Best Practice" (Feb. 2010).

Mölnlycke Health Care brochure, "Trust the evidence: Let clinically relevant evidence of less pain and better overall performance guide your choice of self–adhering absorbent dressings" (Mar. 2010).

Mölnlycke Health Care brochure, "Trust the evidence: Let clinically relevant evidence of less pain and better overall performance guide your choice of self–adhering absorbent dressings" (Aug. 2009).

Mölnlycke Health Care brochure, "A less painful dressing change is something to smile about" (Jun. 2008).

Mölnlycke Health Care brochure, "Mepilex® Border: Less painful and more effective than hydrocolloid dressings" (Jun. 2009).

Mölnlycke Health Care brochure, "Feels as good as it fits" (Jan. 2010).

Mölnlycke's Notice to Admit Facts, Sep. 25, 2009.

Smith & Nephew's Notice to Admit Facts, Sep. 29, 2009.

Court Order, Sep. 30, 2009.

Consent Order, Sep. 30, 2009.

Mölnlycke's List of Documents, Oct. 19, 2009.

Mölnlycke's Admissions, Feb. 8, 2010.

Court Order, Feb. 16, 2010.

Brightwake's First Request for Further Information Made Under Part 18 CPR, Oct. 5, 2009.

Brightwake's Defence and Counterclaim, Oct. 28, 2009.

Brightwake's Grounds of Invalidity, Oct. 28, 2009.

Mölnlycke's Reply and Defence to Counterclaim, Nov. 13, 2009.

Brightwake's Second Request for Further Information Made Under Part 18 CPR.

Mölnlycke's Response to Brightwake's Second Request for Further Information, Jan. 27, 2010.

Mölnlycke's List of Documents, Mar. 11, 2010.

Office Action and Response to Office Action (Chinese), Oct. 9, 2009 and Feb. 22, 2010.

Letter from Mayer Brown International LLP (UK counsel for Mölnlycke Health Care) to Bristows (UK counsel for Smith & Nephew) regarding potential disclosure of certain documents from UK proceedings to the USPTO, Jun. 23, 2010.

Letter from Bristows to Mayer Brown International LLP in response to Jun. 23, 2010 letter from Mayer Brown International LLP, Jul. 1, 2010.

Letter from Mayer Brown International LLP (UK counsel for Mölnlycke Health Care) to Wragge & Co. LLP (UK counsel for Brightwake) regarding potential disclosure of certain documents from UK proceedings to the USPTO, Jun. 23, 2010.

Letter from Wragge & Co. LLP to Mayer Brown International LLP in response to Jun. 23, 2010 letter from Mayer Brown International LLP, Jul. 1, 2010.

English Translation of Counterpart Request for Dismissal, Feb. 4, 2009.

English Translation of Minutes of Oral Hearing, Feb. 17, 2009.

English Translation of Mölnlycke Brief in Support of Complaint, Jun. 24, 2009.

English Translation of Exhibit K2 of Mölnlycke Pleadings—DE 693 11 101 T2, Jan. 18, 1995.

English Translation of Counterpart Appellate Brief, May 5, 2010.

English Translation of Exhibit 17–1 of Counterpart Appellate Brief—German Supreme Court decision, Sep. 18, 2006.

English Translation of Exhibit 17–2 of Counterpart Appellate Brief—German Supreme Court decision, Jul. 10, 2008.

English Translation of Exhibit 19 of Counterpart Appellate Brief—Bank Guarantee of Mölnlycke Health Care AB, Apr. 27, 2010.

Draft Testing Protocol for European Patent 0 251 810 (from Ballard Spahr LLP to Giles Dillingham), Oct. 12, 2009.

Revised Testing Protocol for European Patent 0 251 810 (from Giles Dillingham to Ballard Spahr LLP) Oct. 12, 2009.

Draft Report On the Wound Dressing as Described in European Patent 0 251 810 (from Giles Dillingham to Ballard Spahr LLP), Nov. 2, 2009.

English Translation of Office Action and Response to Office Action, Oct. 9, 2009 and Feb. 22, 2010.

Summons to a Hearing, Jul. 8, 2010.

English Translation of Summons to a Hearing, Jul. 8, 2010.

Notice of Experiments, Jul. 21, 2010.

Penalty Request for Violation of Injunctive Relief (German), Jun. 2, 2010.

Brief Regarding Penalty Request for Violation of Injunctive Relief (German), Jun. 23, 2010.

Exhibit 3 of Penalty Request for Violation of Injunctive Relief—Bank Guarantee (German), Apr. 21, 2010.

Exhibit 4 of Penalty Request for Violation of Injunctive Relief—Defendant's Appeal (German), May 5, 2010.

English Translation of Exhibit 4 of Penalty Request for Violation of Injunctive Relief—Defendant's Appeal, May 5, 2010.

Exhibit 5 of Penalty Request for Violation of Injunctive Relief—Plaintiff's Appellate Requests and Objections to Suspension (German), May 31, 2010.

English Translation of Exhibit 5 of Penalty Request for Violation of Injunctive Relief—Plaintiff's Appellate Requests and Objections to Suspension, May 31, 2010.

Exhibit 6 of Penalty Request for Violation of Injunctive Relief—Invitation to Wound Dressing Roundtable (German), 2010.

Exhibit 7 of Penalty Request for Violation of Injunctive Relief—Smith & Nephew Wound Management Product Catalogue (German), 2010.

Exhibit 8 of Penalty Request for Violation of Injunctive Relief—Smith & Nephew Medical Product Catalogue (German), Sep. 2008.

Exhibit 9 of Penalty Request for Violation of Injunctive Relief—Allevyn Gentle Border Heel Inner Packaging (German), Unspecified.

Exhibit 12 of Penalty Request for Violation of Injunctive Relief—Allevyn Gentle Border Outer Packaging (German), May 2010.

Exhibit 13 of Penalty Request for Violation of Injunctive Relief—Allevyn Gentle Border Inner Packaging (German) May 12, 2010.

Exhibit 14 of Penalty Request for Violation of Injunctive Relief—Allevyn Gentle Border Outer Packaging (German), Mar. 2010.

Exhibit 15 of Penalty Request for Violation of Injunctive Relief—Allevyn Gentle Border Inner Packaging (German), Mar. 30, 2010.

Penalty Request for Not Rendering Account (German), Jun. 15, 2010.

Exhibit 1 of Penalty Request for Not Rendering Account—Letter regarding Enforcement of Mar. 16, 2010 Judgment (English), May 3, 2010.

Exhibit 2 of Penalty Request for Not Rendering Account—E–mail exchange between Vossius & Partner and Quinn Emanuel Urquhart & Sullivan (German) May 11, 2010.

Exhibit 3 of Penalty Request for Not Rendering Account—Letter from Vossius & Partner to Quin Emanuel Urquhart & Sullivan (English), Jun. 22, 2010.

Exhibit 4 of Penalty Request for Not Rendering Account—Letter from Quin Emanuel Urquhart & Sullivan in response to Jun. 22, 2010 Letter from Vossius & Partner (English), Jul. 1, 2010.

Exhibit 5 of Penalty Request for Not Rendering Account—Letter from Quin Emanuel Urquhart & Sullivan to Vossius & Partner in follow–up to Jul. 1, 2010 Letter (English), Jul. 2, 2010.

Exhibit 6 of Penalty Request for Not Rendering Account—Letter from Vossius & Partner to Quin Emanuel Urquhart & Sullivan (English), Jul. 5, 2010.

Exhibit 7 of Penalty Request for Not Rendering Account—Letter from Vossius & Partner to Quin Emanuel Urquhart & Sullivan (English), Jul. 9, 2010.

Appellate Court Decision to Suspend Proceedings (German), Jun. 16, 2010.

English Translation of Appellate Court Decision to Suspend Proceedings, Jun. 16, 2010.

English Translation of Document JJ78 (Penalty Request for Violation of Injunctive Relief), Jun. 2, 2010.

English Translation of JJ79 (Brief Regarding Penalty Request for Violation of Injunctive Relief), Jun. 23, 2010.

English Translation of Document JJ80 (Exhibit 3 of Penalty Request for Violation of Injunctive Relief—Bank Guarantee), Apr. 21, 2010.

English Translation of Document JJ85 (Exhibit 6 of Penalty Request for Violation of Injunctive Relief—Invitation to Wound Dressing Roundtable), 2010.

English Translation of Document JJ86 (Exhibit 7 of Penalty Request for Violation of Injunctive Relief—Smith & Nephew Wound Management Product Catalogue), 2010.

English Translation of Document JJ87 (Exhibit 8 of Penalty Request for Violation of Injunctive Relief—Smith & Nephew Medical Product Catalogue), Sep. 2008.

English Translation of Document JJ88 (Exhibit 9 of Penalty Request for Violation of Injunctive Relief—Allevyn Gentle Border Heel Inner Packaging), Unspecified.

English Translation of Document JJ89 (Exhibit 12 of Penalty Request for Violation of Injunctive Relief—Allevyn Gentle Border Outer Packaging), May 2010.

English Translation of Document JJ90 (Exhibit 13 of Penalty Request for Violation of Injunctive Relief—Allevyn Gentle Border Inner Packaging), May 12, 2010.

English Translation of Document JJ91 (Exhibit 14 of Penalty Request for Violation of Injunctive Relief—Allevyn Gentle Border Outer Packaging), Mar. 2010.

English Translation of Document JJ92 (Exhibit 15 of Penalty Request for Violation of Injunctive Relief—Allevyn Gentle Border Inner Packaging), Mar. 30, 2010.

English Translation of Document JJ93 (Penalty Request for Not Rendering Account), Jul. 15, 2010.

English Translation of Document JJ95 (Exhibit 2 of Penalty Request for Not Rendering Account—E–mail exchange between Vossius & Partner and Quinn Emanuel Urquhart & Sullivan), May 11, 2010.

Notice to Admit filed by Mölnlycke Health Care AB, Sep. 24, 2010.

1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7-11 and 14 is confirmed.

New claims 15-25 are added and determined to be patentable.

Claims 1-6 and 12-13 were not reexamined.

*15. A wound dressing according to claim 7, wherein the dressing is produced by a method which comprises:*

*applying a coating of curable silicone mixture to an upper surface of a perforated carrier material;*

*blowing cold air onto an underside of the coated carrier material so that the silicone mixture is blown away from the perforations in the carrier material so as to form through penetrating perforations and prevent clogging of the perforations in the carrier material; and*

*applying heat to the silicone mixture until it has cured.*

*16. A wound dressing according to claim 7, wherein the dresssing is produced by an apparatus comprising:*

*means for coating an upper surface of the carrier material with a mixture of components which when cured form a silicone gel;*

*an air-blowing unit for blowing cold air onto an underside of the carrier material, said air blowing unit being placed opposite the coating means; and means for delivering heat to the mixture of components applied to the upper surface of the carrier material.*

*17. A wound dressing according to claim 7, wherein the carrier material comprises polyurethane film.*

*18. A wound dressing according to claim 7, further comprising an overlying absorbent pad.*

*19. A wound dressing according to claim 7, further comprising an overlying removable absorbent pad.*

*20. A wound dressing according to claim 7, wherein said carrier material is coated by applying a curable silicone mixture on only one side thereof.*

*21 A wound dressing according to claim 7, comprising a perforated carrier material sheet, wherein said carrier material is coated with silicone gel on only one side of the sheet.*

*22. A wound dressing according to claim 21, wherein said carrier material is coated by applying a curable silicone mixture on only one side of the sheet.*

*23. A wound dressing according to claim 21, wherein the carrier material has from about 0.5 to about 200 perforations per $cm^2$, said perforations having a diameter ranging from about 0.1 to about 2 mm.*

*24. A wound dressing according to claim 7, wherein the coated carrier consists essentially of the perforated carrier material and the layer of hydrophobic silicone gel.*

*25. A wound dressing according to claim 7, wherein the coated carrier consists of the perforated carrier material and the layer of hydrophobic silicone gel.*

\* \* \* \* \*

(12) EX PARTE REEXAMINATION CERTIFICATE (8393rd)
United States Patent
Fabo

(10) Number: US 5,635,201 C2
(45) Certificate Issued: Jul. 5, 2011

(54) METHOD AND AN ARRANGEMENT FOR MANUFACTURING WOUND DRESSINGS, AND A WOUND DRESSING MANUFACTURED IN ACCORDANCE WITH THE METHOD

(75) Inventor: Tomas Fabo, Mölnlycke (SE)

(73) Assignee: Molnlycke Health Care AB, Gothenburg (SE)

Reexamination Request:
No. 90/011,259, Sep. 30, 2010

Reexamination Certificate for:
Patent No.: 5,635,201
Issued: Jun. 3, 1997
Appl. No.: 08/302,875
Filed: Sep. 14, 1994

Reexamination Certificate C1 5,635,201 issued Feb. 15, 2011

(22) PCT Filed: Mar. 30, 1993

(86) PCT No.: PCT/SE93/00270

§ 371 (c)(1),
(2), (4) Date: Sep. 14, 1994

(87) PCT Pub. No.: WO93/19709

PCT Pub. Date: Oct. 14, 1993

(51) Int. Cl.
*A61F 13/00* (2006.01)
*A61F 13/02* (2006.01)

(52) U.S. Cl. .................. 424/443; 424/449; 427/2.31; 427/348; 602/47

(58) Field of Classification Search .............. 424/443
See application file for complete search history.

(56) References Cited

U.S. PATENT DOCUMENTS

| 3,671,483 A | 6/1972 | Young |
| 3,800,792 A | 4/1974 | McKnight et al. |
| 3,888,247 A | 6/1975 | Stenvall |
| 4,747,895 A | 5/1988 | Wallerstein et al. |
| 4,921,704 A | 5/1990 | Fabo |
| 4,946,853 A | 8/1990 | Bannon et al. |
| 4,991,574 A | 2/1991 | Pocknell |
| 4,995,382 A | 2/1991 | Lang et al. |
| 5,322,729 A | 6/1994 | Heeter et al. |

FOREIGN PATENT DOCUMENTS

| GB | 713838 | 8/1954 |
| GB | 830177 | 3/1960 |

OTHER PUBLICATIONS

Quinn, Karen J., Thesis submitted for the degree of Doctor of Philosphy, "The Application of Silicone Gel for Treatment of Hypertrophic Scars and Burn Wounds, and Consideration of the 'Ideal' Burn Dressing" Bioengineering Unit, University of Strathclyde, Glasgow, Scotland, Apr. 1, 1986.
Perkins, K. et al., "Silicone gel: a new treatment for burn scars and contractures," The Burns Unit, The Adelaide Children's Hospital, South Australia, vol. 9, pp. 201–204, 1983.
Sawada, Y., "Ideas and Innovations: Silicone gel sheet tie–over for skin graft on the eyelid following release of scar contracture," British Journal of Plastic Surgery, vol. 41, pp. 325–326, 1988.

*Primary Examiner*—Gary L. Kunz

(57) ABSTRACT

A method and apparatus for manufacturing a wound dressing, and a wound dressing produced thereby. The upper surface of a perforated carrier material (2) is coated with a curable silicone mixture (3) and cold air is blown onto the underside of the coated carrier material. Heat is then applied to the silicone mixture until it has cured to a silcone gel.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4, 7-12 and 14-25 is confirmed.

Claims 5, 6 and 13 were not reexamined.

* * * * *